US008088069B2

(12) United States Patent
Sabata

(10) Patent No.: US 8,088,069 B2
(45) Date of Patent: Jan. 3, 2012

(54) ULTRASONIC DOPPLER DIAGNOSIS DEVICE

(75) Inventor: Tomohiro Sabata, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 910 days.

(21) Appl. No.: 11/958,810

(22) Filed: Dec. 18, 2007

(65) Prior Publication Data

US 2008/0154134 A1    Jun. 26, 2008

(30) Foreign Application Priority Data

Dec. 22, 2006 (JP) ................ 2006-346271
Sep. 21, 2007 (JP) ................ 2007-245696

(51) Int. Cl.
*A61B 8/00* (2006.01)
(52) U.S. Cl. ........ 600/437; 600/438; 600/443; 600/453; 600/454; 600/455; 600/457
(58) Field of Classification Search ............. 600/437, 600/438, 443, 453, 454, 455, 457
See application file for complete search history.

(56) References Cited

U.S. PATENT DOCUMENTS

| 4,930,514 | A | 6/1990 | Baba et al. | |
|---|---|---|---|---|
| 5,083,566 | A | 1/1992 | Baba | |
| 5,429,137 | A | 7/1995 | Phelps et al. | |
| 6,571,020 | B1 * | 5/2003 | Dumoulin et al. | ............ 382/254 |

FOREIGN PATENT DOCUMENTS

| JP | 4-161146 | 6/1992 |
|---|---|---|
| JP | 09-187458 | 7/1997 |
| JP | 2678124 | 7/1997 |

OTHER PUBLICATIONS

Extended European Search Report dated Mar. 1, 2010.
English-language abstract only of Japanese Patent Application Publication No. 06-205774 dated Jul. 26, 1994.

* cited by examiner

*Primary Examiner* — James Kish
(74) *Attorney, Agent, or Firm* — Scully, Scott, Murphy & Presser, P.C.

(57) ABSTRACT

An ultrasonic Doppler diagnosis device having a velocity data interpolating section for generating interpolated velocity data for interpolating velocity data between two sound lines and two scanning lines, using the velocity data at the intersections. The velocity data interpolating section converts two scalar arrays of unsigned numeric data corresponding to a first and second numeric values to signed arrays of numeric data using a data converting section and generates the interpolated velocity data based on the converted signed array of numeric data, when a result of identification obtained from an identifying section indicates that one of the first and second numeric values has a positive velocity smaller than a first threshold value corresponding to a positive velocity, and the other of the first and second numeric values has a negative velocity greater than a second threshold value corresponding to a negative velocity.

2 Claims, 10 Drawing Sheets

UNSIGNED NUMERIC DATA
SCALAR ARRAY
ARGUMENT

SIGNED NUMERIC DATA
COLOR PALETTE ARRAY
ARGUMENT

US 8,088,069 B2

ULTRASONIC DOPPLER DIAGNOSIS DEVICE

CROSS REFERENCE TO RELATED APPLICATION

This application claims benefit of Japanese Application No. 2006-346271 filed in Japan on Dec. 22, 2006, and, No. 2007-245696 filed in Japan on Sep. 21, 2007, the contents of which are incorporated by this reference.

BACKGROUND OF THE INVENTION

1. Field of the Invention

The present invention relates to an ultrasonic Doppler diagnosis device for measuring the velocity of a kinetic reflector such as a blood flow within a living body.

2. Description of the Related Art

An ultrasonic Doppler diagnosis device has been known for measuring a blood flow velocity within a living body, for example. When such an ultrasonic Doppler diagnosis device displays a two-dimensional Doppler view to represent spatial distribution of a velocity of a kinetic reflector such as a blood flow, the device passes a Doppler shift signal through an autocorrelator, obtains an average frequency from complex output data from the autocorrelator by an operation, and spatially interpolates the calculated average frequency for display.

However, there is a problem in that for frequency aliasing caused around a Nyquist frequency decided depending on a sampling frequency of a Doppler shift signal, a maximum value of a positive velocity (bright red) and a maximum value of a negative velocity (bright blue) are averaged, so that an average frequency is interpolated in incorrect data (a dark color with a velocity being approximately 0) where bright blue or bright red should be interpolated in the correct way.

In order to solve the problem as above, for example, Japanese Patent Laid-Open No. 2678124 proposes an ultrasonic Doppler diagnosis device to solve disadvantages of data interpolation due to frequency aliasing by obtaining complex interpolation data of each pixel between scanning lines and by operating velocity data from an argument of the complex interpolation data.

SUMMARY OF THE INVENTION

An ultrasonic Doppler diagnosis device according to the present invention comprises: ultrasonic transceiver means for emitting and scanning an ultrasonic wave and for transmitting and receiving the wave to a kinetic reflector; velocity data calculating means for extracting a Doppler shift signal using an ultrasonic signal from the kinetic reflector transmitted and received by the ultrasonic transceiver means, and for calculating velocity data at an intersection of a sound line and a scanning line of the kinetic reflector; velocity data interpolating means for interpolating the velocity data between the sound line and the scanning line and generating the interpolated velocity data; and color image generating means for generating a color flow mapping image of the kinetic reflector based on the velocity data and the interpolated velocity data, in which the velocity data interpolating means includes numeric value determining means for determining a plurality of values of the velocity data and the interpolated velocity data, and if a result of the determination is a pre-determined determination result based on the determination result of the numeric value determining means, the velocity data and the interpolated velocity data are converted to a first numeric value array to generate interpolated velocity data.

DETAILED DESCRIPTION OF THE PREFERRED EMBODIMENTS

The following will describe an embodiment of the present invention with reference to the drawings.

First Embodiment

Figure 1:
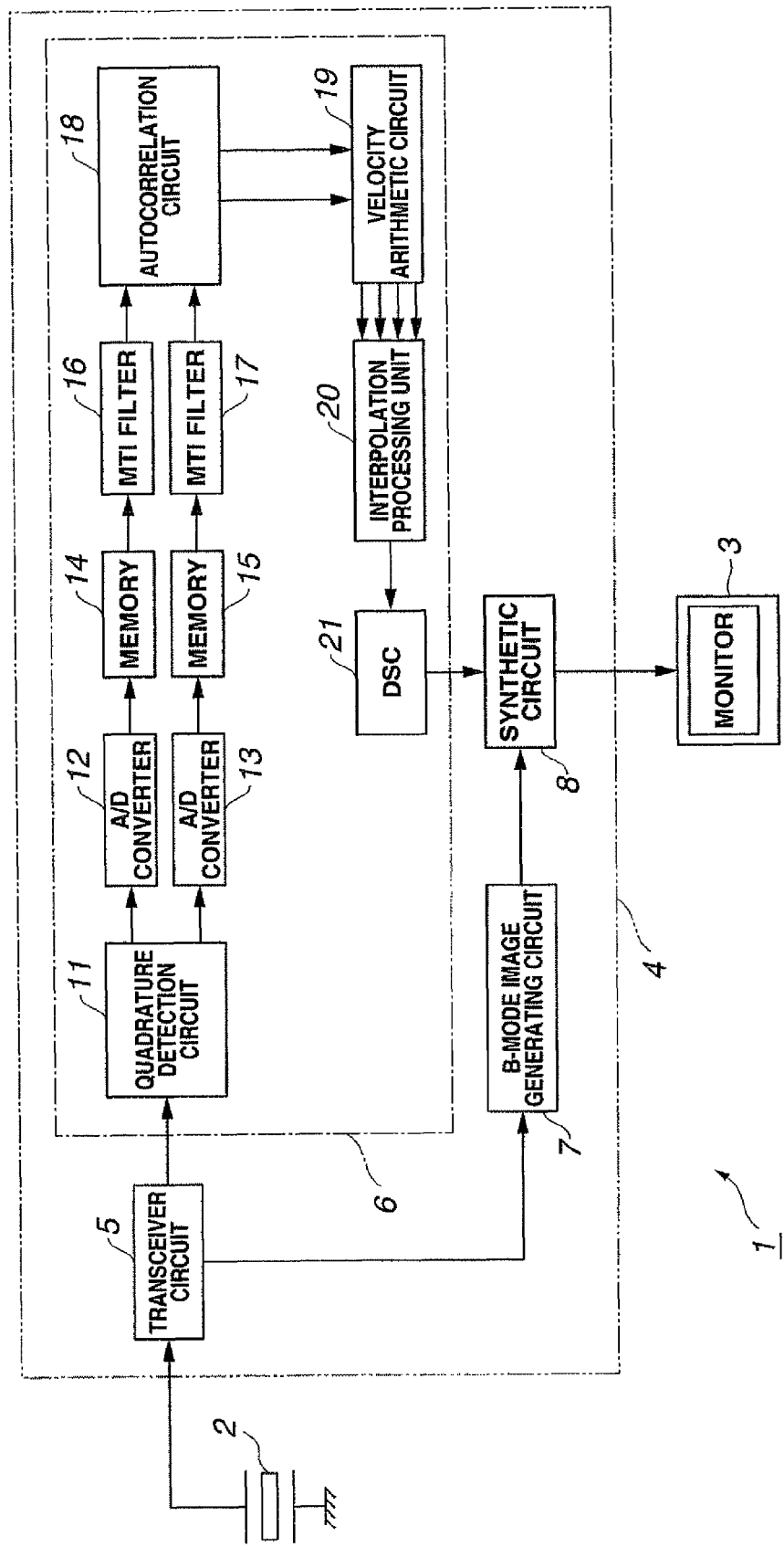
FIG. 1 is a configuration diagram showing configuration of an ultrasonic Doppler diagnosis device according to a first embodiment of the present invention.
Figure 2:
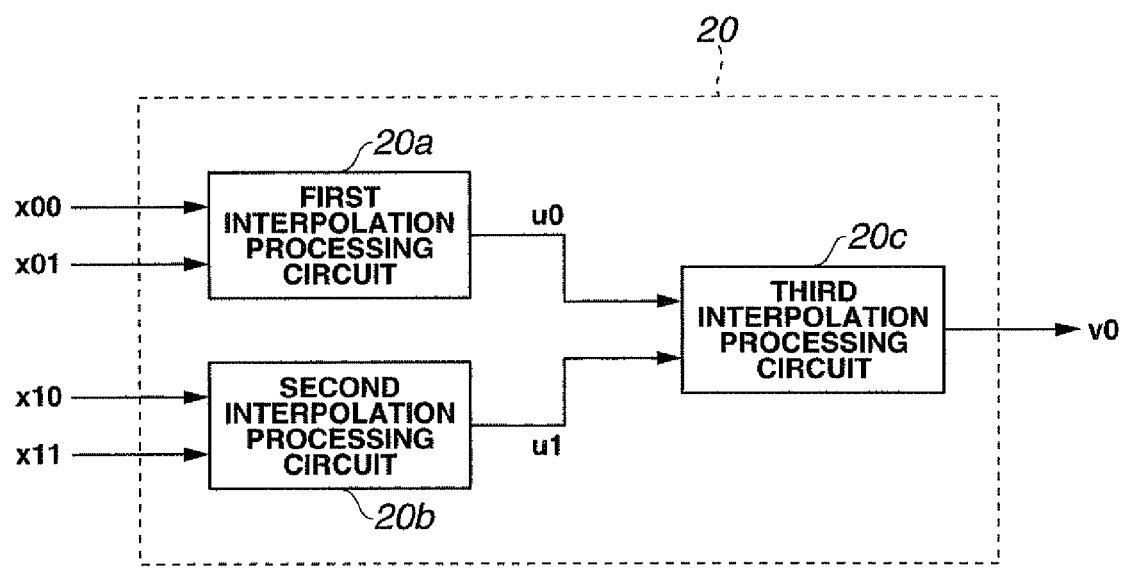
FIG. 2 is a block diagram showing configuration of an interpolation processing unit in FIG. 1.
Figure 3:
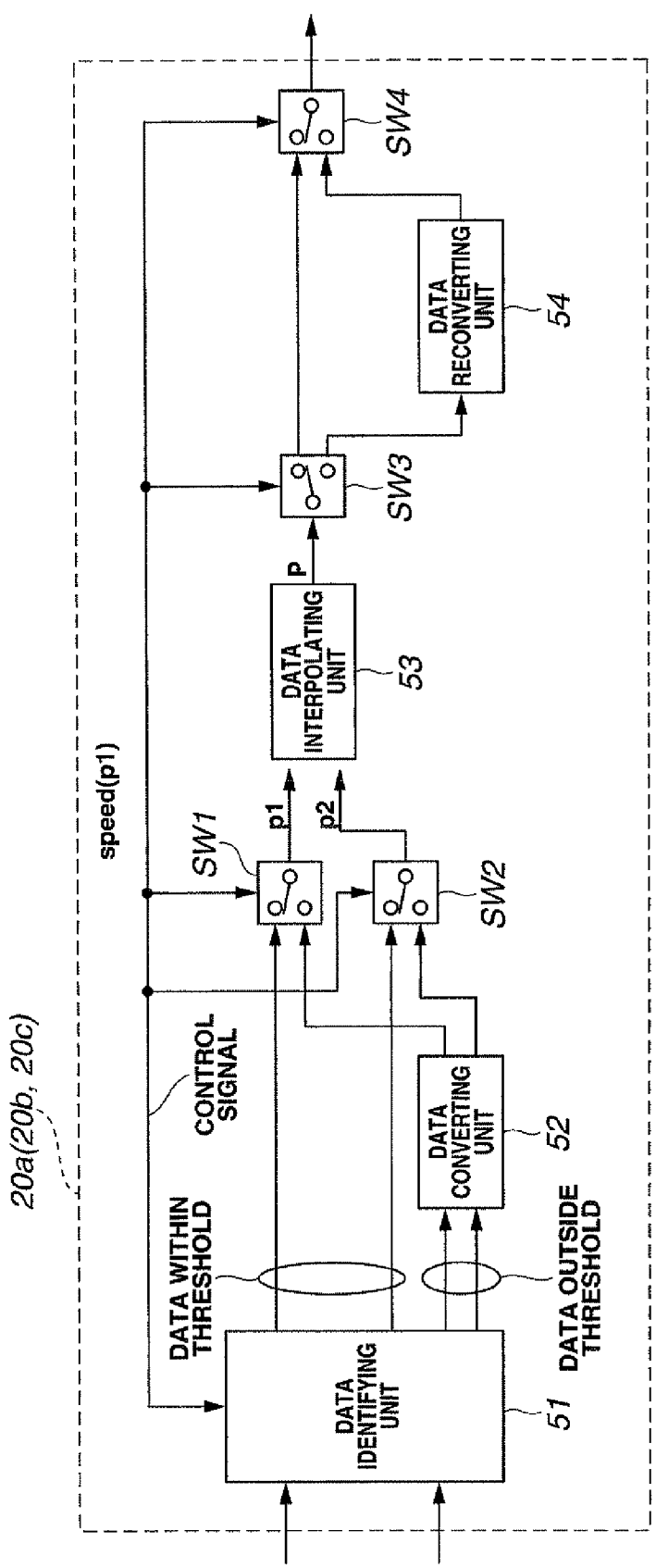
FIG. 3 is a block diagram showing configuration of first to third interpolation processing circuits in FIG. 2.
Figure 4:
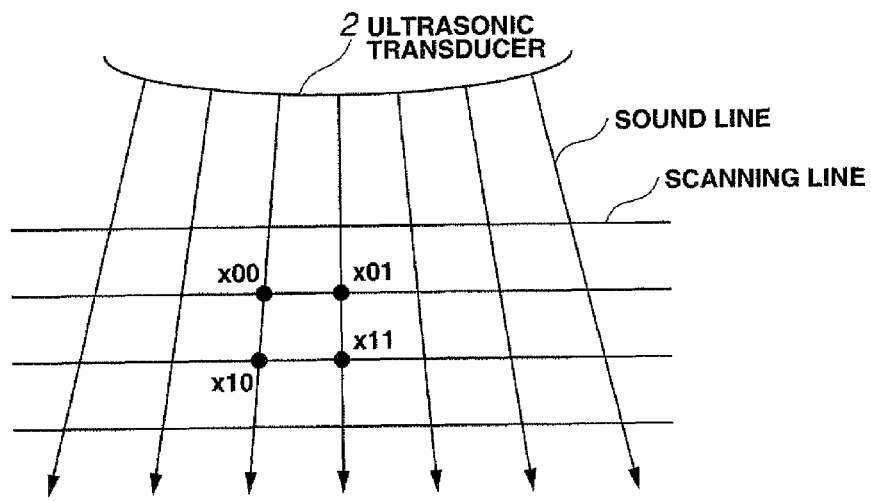
FIG. 4 is a first illustrative drawing illustrating action of the interpolation processing unit in FIG. 2.
Figure 5:
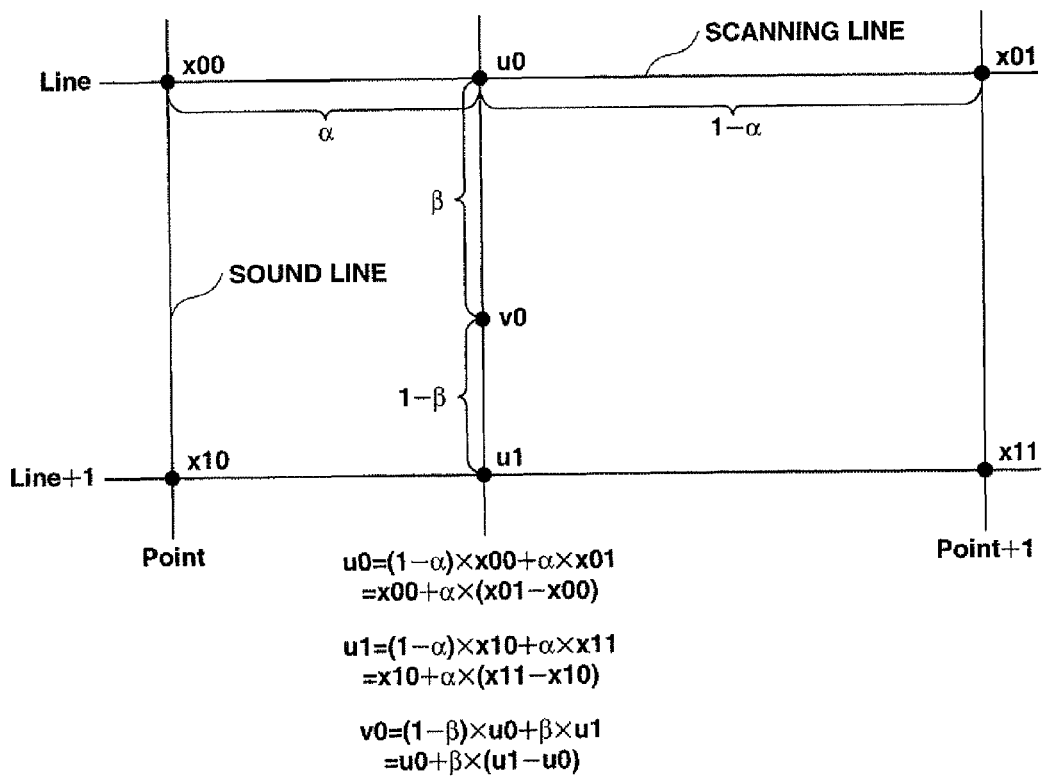
FIG. 5 is a second illustrative drawing illustrating the action of the interpolation processing unit in FIG. 2.
Figure 6:
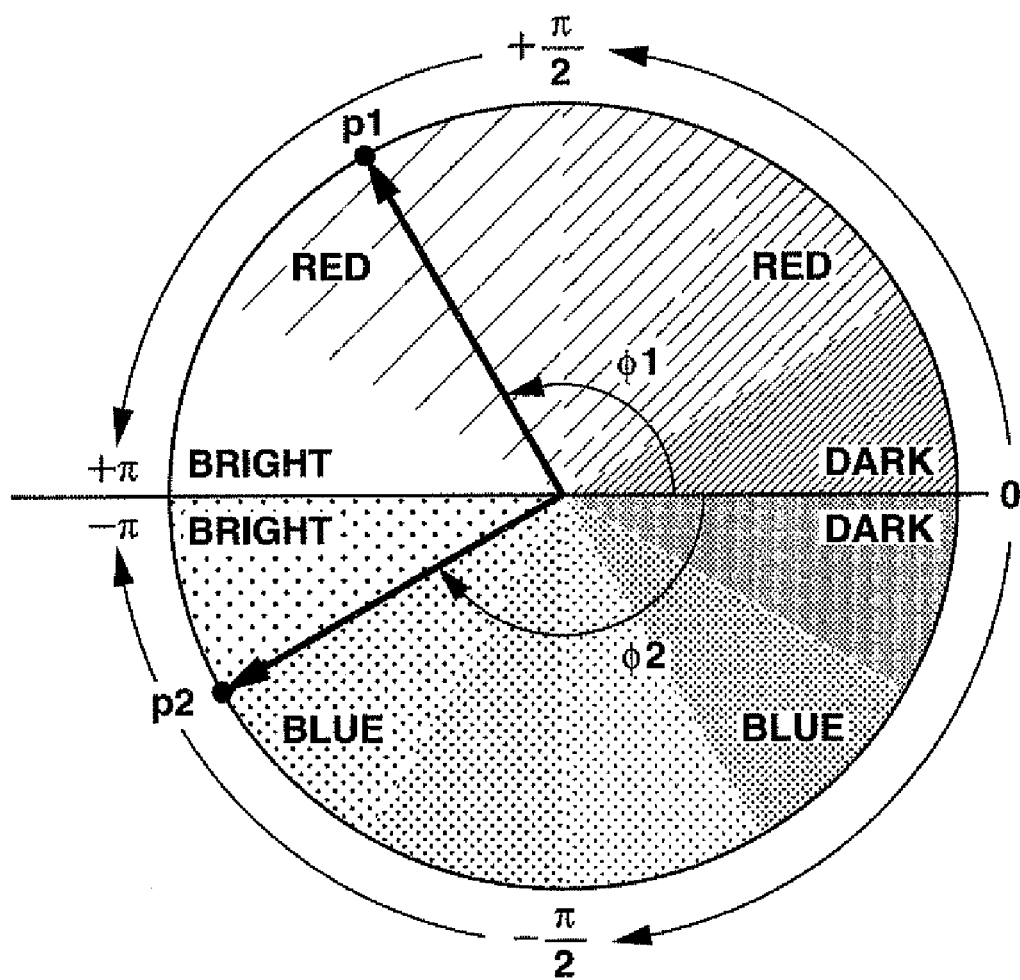
FIG. 6 is a drawing illustrating an example of color palette array representation of velocity data of the ultrasonic Doppler diagnosis device in FIG. 1.
Figure 7:
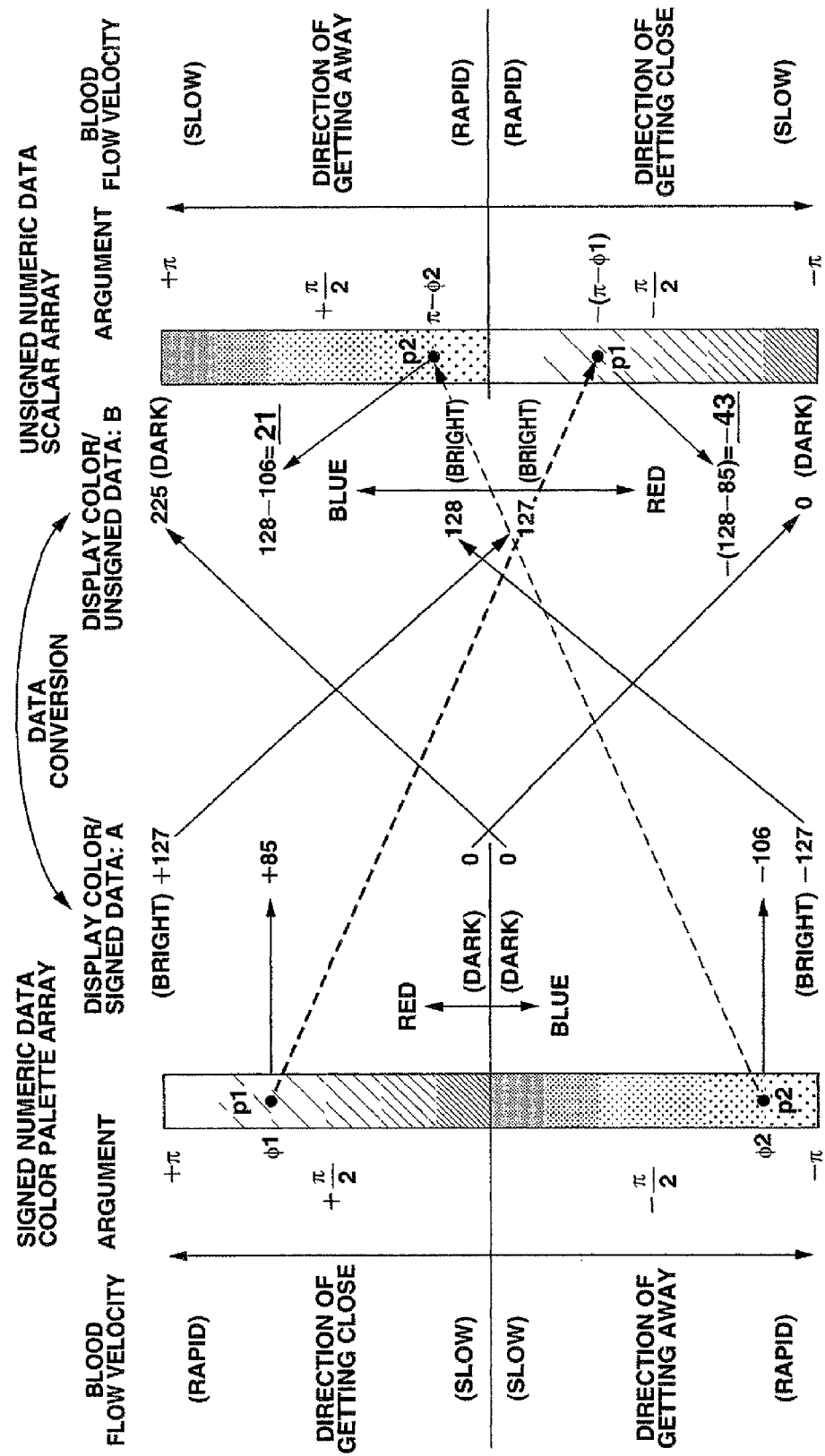
FIG. 7 is a drawing illustrating conversion of representation between the scalar array representation and the color palette array representation of the velocity data in FIG. 6.
Figure 8:
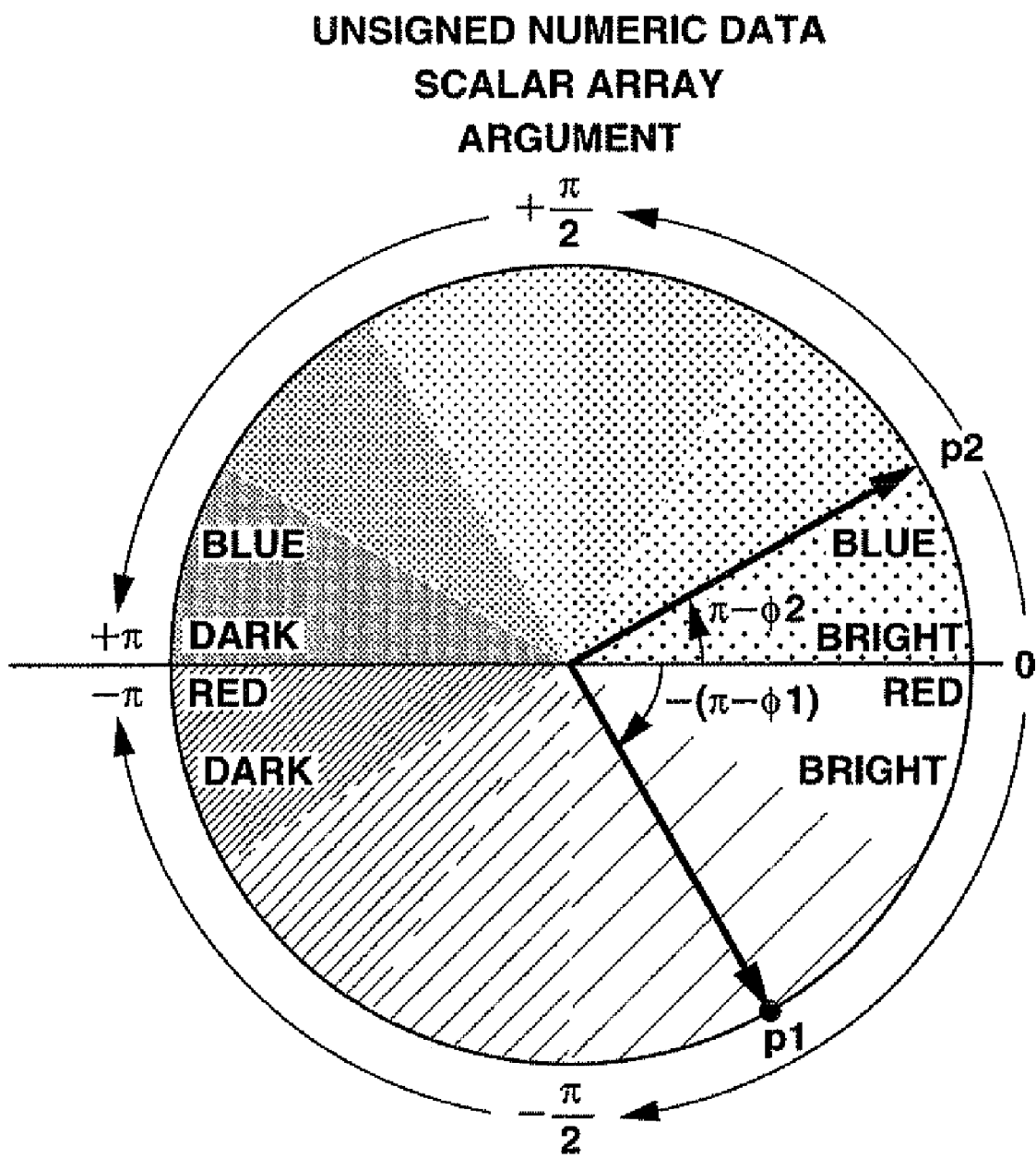
FIG. 8 is a drawing illustrating an example of scalar array representation of velocity data by the representation conversion in FIG. 7.
Figure 9:
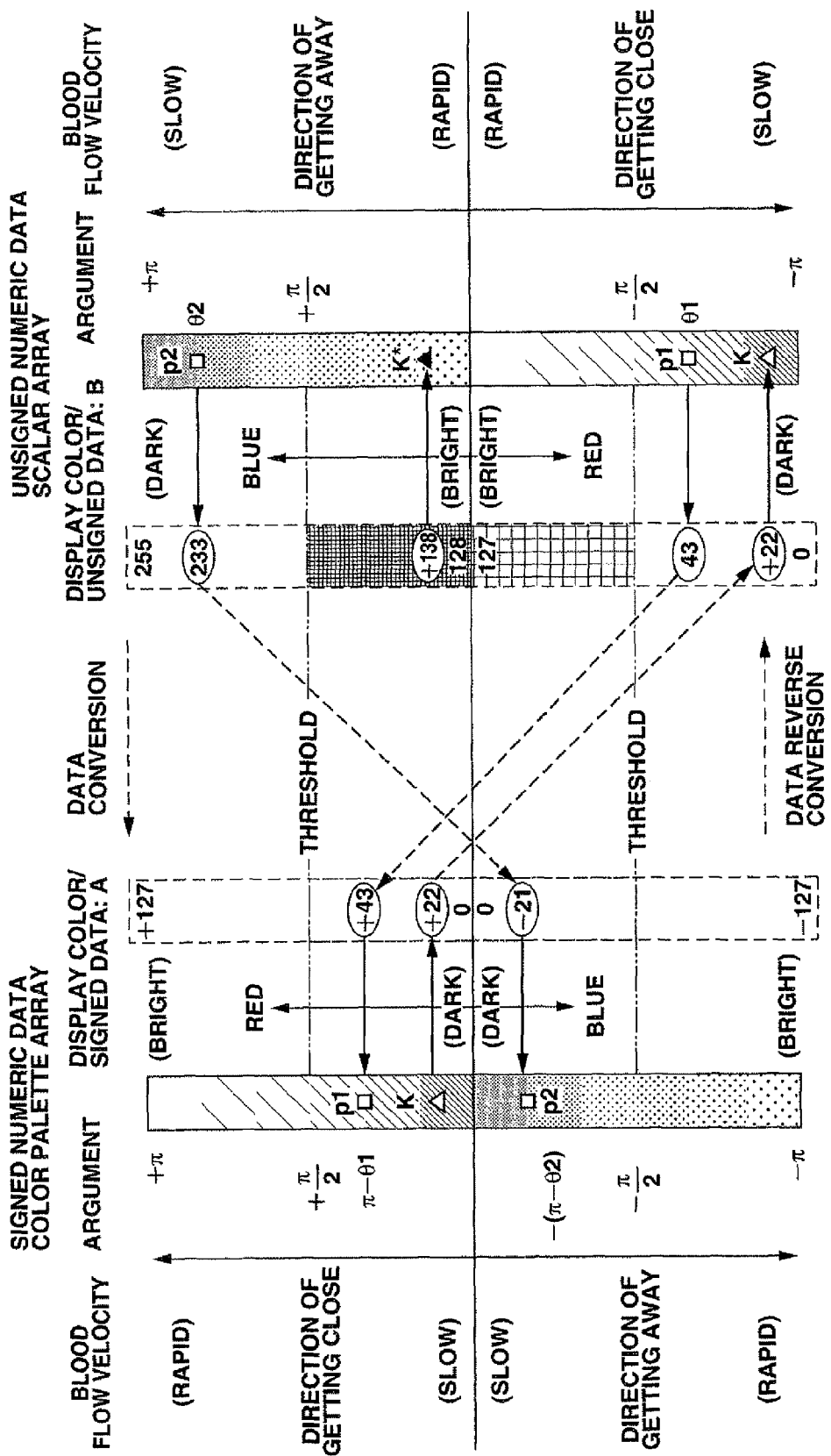
FIG. 9 is a first illustrative drawing illustrating action of the first interpolation processing circuit in FIG. 3.
Figure 10:
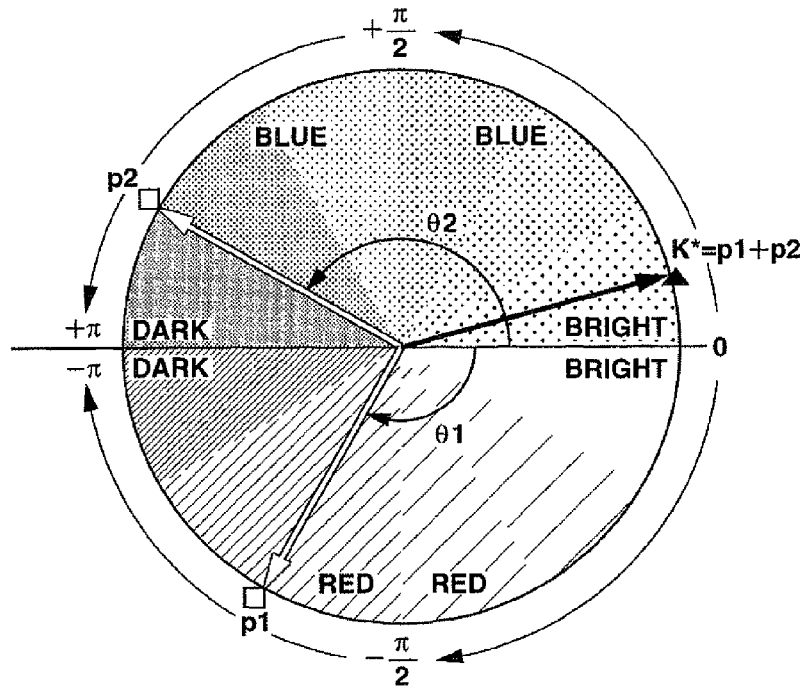
FIG. 10 is a second illustrative drawing illustrating action of the first interpolation processing circuit in FIG. 3.
Figure 11:
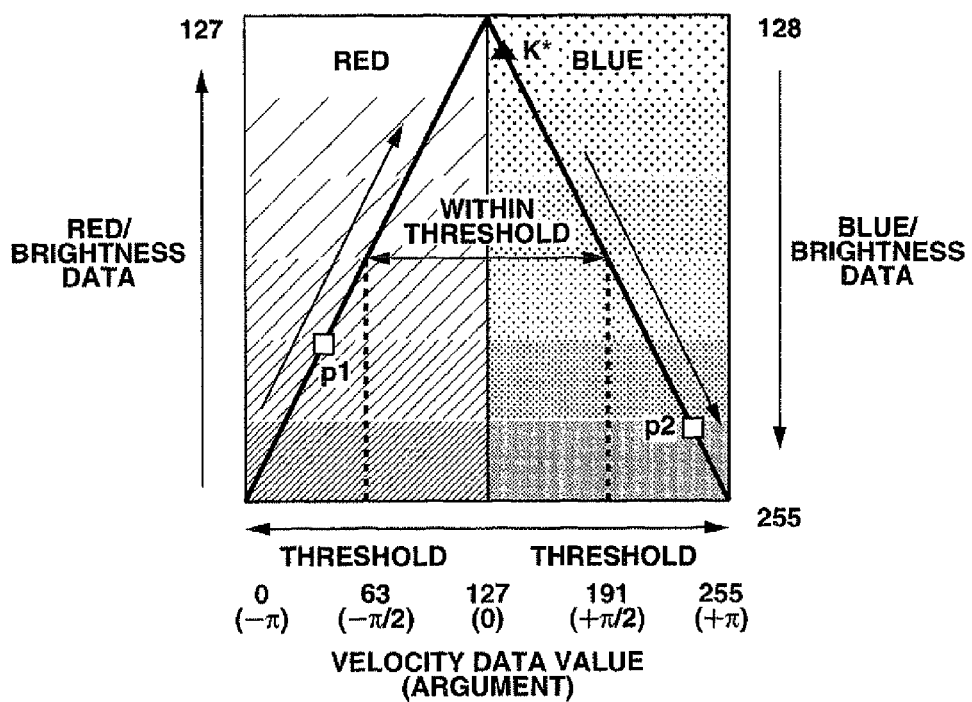
FIG. 11 is a third illustrative drawing illustrating action of the first interpolation processing circuit in FIG. 3.
Figure 12:
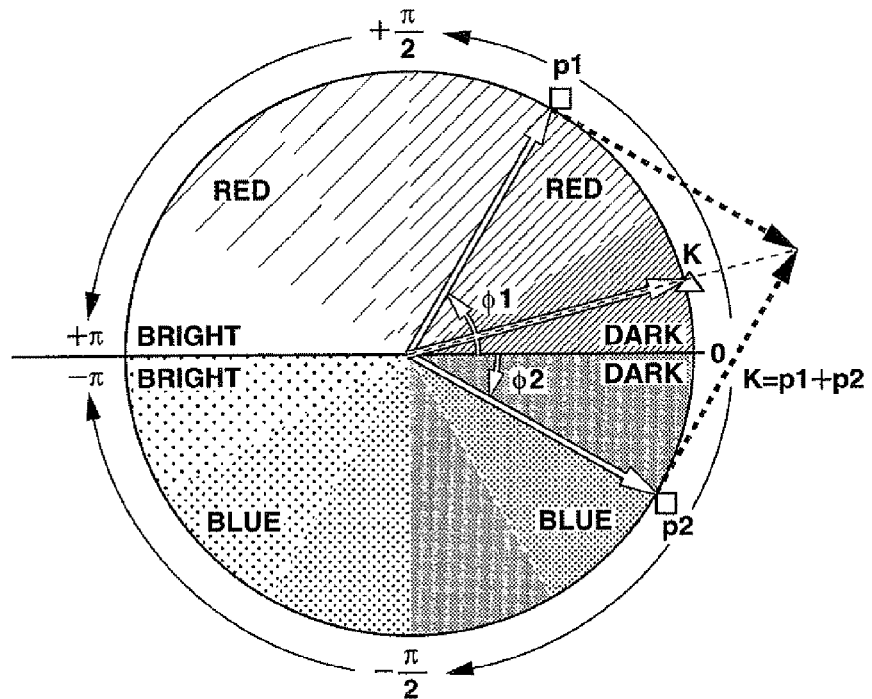
FIG. 12 is a fourth illustrative drawing illustrating action of the first interpolation processing circuit in FIG. 3.
Figure 13:
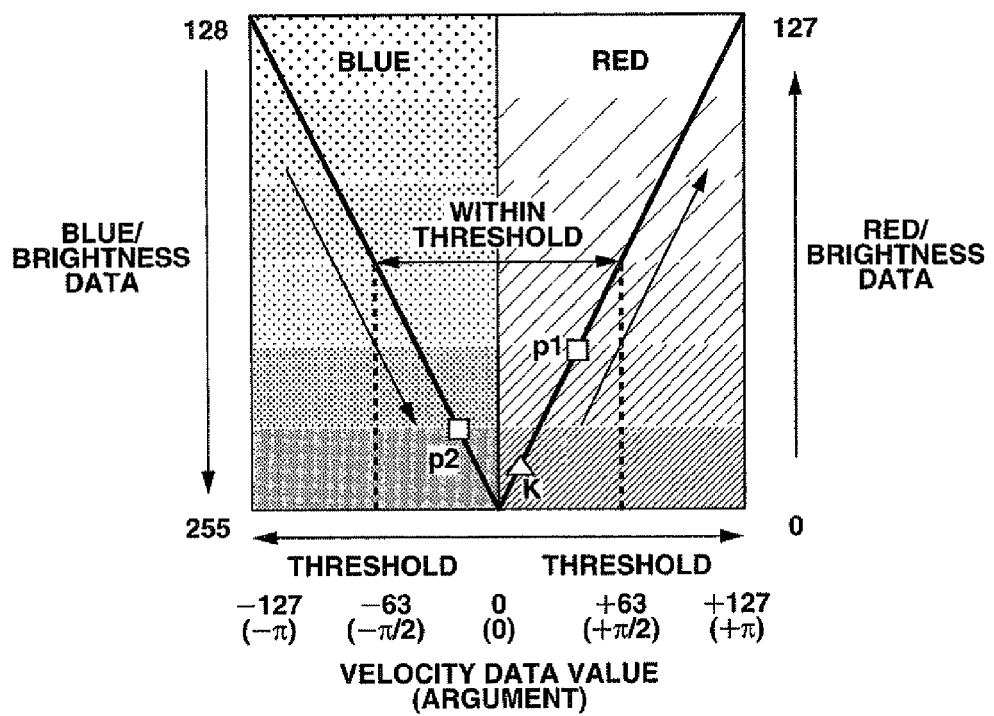
FIG. 13 is a fifth illustrative drawing illustrating action of the first interpolation processing circuit in FIG. 3.

FIGS. 1 to 13 relate to a first embodiment of the present invention. FIG. 1 is a configuration diagram showing configuration of an ultrasonic Doppler diagnosis device. FIG. 2 is a block diagram showing configuration of an interpolation processing unit in FIG. 1. FIG. 3 is a block diagram showing configuration of first to third interpolation processing circuits in FIG. 2. FIG. 4 is a first illustrative drawing illustrating action of the interpolation processing unit in FIG. 2. FIG. 5 is a second illustrative drawing illustrating the action of the interpolation processing unit in FIG. 2. FIG. 6 is a drawing illustrating an example of color palette array representation of velocity data of the ultrasonic Doppler diagnosis device in FIG. 1. FIG. 7 is a drawing illustrating conversion of representation between the scalar array representation and the color palette array representation of the velocity data in FIG. 6. FIG. 8 is a drawing illustrating an example of scalar array representation of velocity data by the representation conversion in FIG. 7. FIG. 9 is a first illustrative drawing illustrating action of the first interpolation processing circuit in FIG. 3. FIG. 10 is a second illustrative drawing illustrating action of the first interpolation processing circuit in FIG. 3. FIG. 11 is a third illustrative drawing illustrating action of the first interpolation processing circuit in FIG. 3. FIG. 12 is a fourth illustrative drawing illustrating action of the first interpolation processing circuit in FIG. 3. FIG. 13 is a fifth illustrative drawing illustrating action of the first interpolation processing circuit in FIG. 3.

As shown in FIG. 1, an ultrasonic Doppler diagnosis device 1 according to the present embodiment includes a probe 2 for transmitting and receiving an ultrasonic wave to/from a living body (not shown). The probe 2 connects to a transceiver circuit 5 for transmitting an electric signal to the living body (not shown) in a pre-determined repeating cycle, and for receiving a received signal of the probe 2 that receives a reflected wave reflected by a kinetic reflector such as a blood flow within the living body.

The transceiver circuit 5 herein is configured to scan an ultrasonic pulse beam emitted from the probe 2 by mechanical or electrical angle deflection, for example, and to periodically scan a living body by the ultrasonic pulse beam or to stop the scan by a desired deflection angle.

The ultrasonic Doppler diagnosis device 1 further comprises a B-mode image generating circuit 7 for detecting a received signal received by the transceiver circuit 5 and generating a B-mode image, a Doppler image generating unit 6 for generating a Doppler image by color flow mapping (CFM), and a synthetic circuit 8 for displaying a synthesized image on a monitor, in which the synthesized image is produced by synthesization of the B-mode image and the Doppler image.

The Doppler image generating unit 6 includes a quadrature detection circuit 11 for assigning the received signal received by the transceiver circuit 5 to orthogonal coordinates. The quadrature detection circuit 11 connects to A/D converters 12 and 13 for converting an output of the quadrature detection circuit 11 to digital data.

The quadrature detection circuit 11 herein performs known quadrature detection processing on an inputted analog signal to output two signals that include only shift frequencies and have phases differing from each other by 90° to the A/D converters 12 and 13.

The ultrasonic Doppler diagnosis device 1 also includes, in post-stages of the A/D converters 12 and 13, memories 14 and 15 that store the converted digital data, MTI (Moving Target Indicator) filters 16 and 17 for removing a component that moves at a low velocity such as a living body from the digital data stored in the memories 14 and 15 using known processing, and for outputting I data (In Phase data) and Q data (Quadrature data) of a kinetic reflector, and an autocorrelation circuit 18 for performing complex autocorrelation processing on the I data and Q data from the MTI filters 16 and 17.

The Doppler image generating unit 6 further comprises a velocity arithmetic circuit 19 for calculating the velocity of a blood flow, for example, from the processed signal subjected to the complex autocorrelation processing by the autocorrelation circuit 18, an interpolation processing unit 20 for interpolating the velocity data calculated by the velocity arithmetic circuit 19, and a DSC (digital scan converter) 21 for converting a value of the velocity data from the interpolation processing unit 20 to a brightness value depending on the velocity to output a Doppler color image to the synthetic circuit 8.

The interpolation processing unit 20 is configured by three interpolation processing circuits, i.e., first to third interpolation processing circuits 20a, 20b and 20c, as shown in FIG. 2. The interpolation processing unit 20 will be described later in detail.

Each of the first to third interpolation processing circuits 20a, 20b and 20c is configured by a data identifying unit 51, a data converting unit 52, a data interpolating unit 53, a data reconverting unit 54 and four switches SW1 to SW4, as shown in FIG. 3. The first to third interpolation processing circuits 20a, 20b and 20c will be described later in detail.

Next, action of the present embodiment configured as described in the above will be described. The ultrasonic Doppler diagnosis device 1 according to the present embodiment transmits an ultrasonic pulse from the transceiver circuit 5 via the probe 2 in a pre-determined repeating cycle, and receives a reflected wave emitted from the transceiver circuit 5 and reflected by a kinetic reflector such as a blood flow.

The reflected wave received by the transceiver circuit 5 is further detected by the quadrature detection circuit 11. A Doppler shift signal detected by the quadrature detection circuit 11 is digitized by the A/D converters 12 and 13 and stored in the memories 14 and 15.

Then, I data (In Phase data) and Q data (Quadrature data) of a kinetic reflector are extracted from the Doppler shift signal stored in the memories 14 and 15 by the MTI filters 16 and 17, and sent to the autocorrelation circuit 18. The autocorrelation circuit 18 obtains an argument from the I data and Q data, and outputs calculated argument data to the velocity arithmetic circuit 19. The velocity arithmetic circuit 19 calculates velocity data of a kinetic reflector such as a blood flow from the argument data, and outputs the calculated velocity data to the interpolation processing unit 20.

The interpolation processing unit 20 performs interpolation processing on the velocity data, as described later. An output from the interpolation processing unit 20 is converted to two-dimensional coordinates by the DSC 21, synthesized with a B-mode image from the B-mode image generating circuit 7 by the synthetic circuit 8, and displayed on a monitor 3.

The interpolation processing unit 20 will be described herein. Suppose that velocity data at intersections where sound lines and scanning lines intersect are x00, x01, x10 and x11, as shown in FIG. 4. First, the interpolation processing unit 20 calculates velocity data u0 at a position (coordinates) between the intersections from velocity data: x00 of an intersection (sound line position, scanning line position) (Line, Point) and velocity data: x01 of an intersection (sound line position, scanning line position)=(Line, Point+1) in the first interpolation processing circuit 20a by the first to third interpolation processing circuit 20a, 20b and 20c (see FIG. 2) by performing interpolation operation using the following equation (1) by interpolation processing, as shown in FIG. 5.

$$u0=(1-\alpha)\times x00+\alpha \times x01=x00+\alpha \times (x01-x00) \quad (1)$$

Similarly, the second interpolation processing circuit 20b calculates velocity data u1 at a position (coordinates) between the intersections from velocity data: x10 of an intersection (sound line position, scanning line position)=(Line+1, Point) and velocity data: x11 of an intersection (sound line position, scanning line position)=(Line+1, Point+1) by performing interpolation operation using the following equation (2) by interpolation processing.

$$u1=(1-\alpha)\times x10+\alpha \times x11=x10+\alpha \times (x11-x10) \quad (2)$$

Then, the third interpolation processing circuit 20c performs interpolation processing on the velocity data u0 and the velocity data u1, and calculates velocity data v0 between the velocity data u0 and the velocity data u1 by performing interpolation operation using the following equation (3):

$$v0=(1-\beta)\times u0+\beta \times u1=x00+\beta \times (u1-u0) \quad (3)$$

In the above equations, $\alpha$ is a correction coefficient at a sound line position and $\beta$ is a correction coefficient at a scanning line position.

As described in the above, the velocity arithmetic circuit 19 calculates velocity data of a kinetic reflector such as a blood flow from argument data. Conceptually describing, if complex vectors P1 and P2 including I data and Q data of a kinetic reflector are as shown in FIG. 6, velocity data k1 and k2 are calculated from arguments $\phi 1$ and $\phi 2$ of the respective complex vectors P1 and P2.

Specifically, according to standard ultrasonic Doppler display, if a blood flow gets close at an intersection (sound line position, scanning line position), velocity data is represented in red; if a blood flow gets away, velocity data is represented in blue; and a level of the velocity is represented by brightness, as shown in FIG. 7. Meanwhile, argument data contains sign information indicating positive or negative in the highest-order bit of the data, so that argument data in a red region is represented correspondently to 0 to $+\pi$ in the brightness: dark to bright, while argument data in a blue region is represented correspondently to 0 to $-\pi$ in brightness: dark to bright.

Hereinafter, such an array of signed numeric data (a left array in FIG. 7) is referred to as a color palette array.

On the other hand, the velocity arithmetic circuit 19 does not handle the highest-order bit as a sign contrary to the argument data containing a sign, but as a numeric value to calculate velocity data. Specifically, if argument data is $-\pi/2$ (in a blue region), for example, then a highest-order bit indicating a sign is "1" so that velocity data as numeric value data containing a sign is "−63", while velocity data considering a sign as a part of a numeric value is "191". If argument data is $+\pi/2$ (in a red region), then a highest-order bit indicating a sign is "0" so that velocity data as numeric value data containing a sign is "+63", while velocity data considering a sign as a part of a numeric value is "63". Argument data is represented as an array of unsigned numeric data (hereinafter, a scalar array) as shown in a right side in FIG. 7 based on unsigned numeric data being velocity data considering a sign as a part of a numeric value. The velocity arithmetic circuit 19 handles unsigned numeric data of the scalar array as velocity data.

The complex vectors P1 and P2 based on the scalar array are shown in FIG. 8. In FIG. 8, arguments ($\phi 1$, $\phi 2$) of the complex vectors P1 and P2 shown in FIG. 6 are represented as arguments $(-(\pi-\phi 1), \pi-\phi 2)$.

Hereinafter, a numeric value representing velocity data considering a sign as a part of a numeric value (unsigned numeric data) is underlined. Meanwhile, a numeric value representing numeric value data containing a sign (signed numeric data) is attached with a sign (+ or −).

As shown in FIG. 9, if one of two velocity data is a value of 233 within "192 to 255 ($+\pi/2$ to $+\pi$): darker blue side", for example, and the other is a value of 43 within "0 to 63 ($-\pi$ to $-\pi/2$): darker red side", for example, in a scalar array, then when the first interpolation processing circuit 20a of the interpolation processing unit 20 performs interpolation processing on the two velocity data, a value of 131 is calculated as a result of the interpolation. The result is different from a result of interpolation based on the original vector operation, as shown in FIGS. 10 and 11.

The above description is not limited to the first interpolation processing circuit 20a, but the second and third interpolation processing circuits 20b and 20c also act similarly. Hereinafter, the first interpolation processing circuit 20a will be described as an example.

According to the present embodiment, as shown in FIG. 9, the first interpolation processing circuit 20a judges whether or not one of velocity data of two inputted scalar arrays is a value of "192 to 255 ($+\pi/2$ to $+\pi$): darker blue side" and the other is a value of "0 to 63 ($-\pi$ to $-\pi/2$): darker red side" by the data identifying unit 51 (see FIG. 3).

If the circuit 20a judges one is a value of "192 to 255 ($+\pi/2$ to $+\pi$): darker blue side" and the other is a value of "0 to 63 ($-\pi$ to $-\pi/2$): darker red side", the data identifying unit 51 (see FIG. 3) controls the switches SW1 to SW4 (see FIG. 3) to convert two scalar arrays of velocity data to color palette arrays of velocity data by the data converting unit 52 (see FIG. 3), and outputs the result to the data interpolating unit 53 (see FIG. 3). In that case, the data interpolating unit 53 interpolates the velocity data based on vector operation on complex spaces in the color palette arrays, as shown in FIGS. 12 and 13. Then, based on the velocity data interpolated in the data interpolating unit 53, the data reconverting unit 54 (see FIG. 3) reversely converts the velocity data from the color palette arrays to scalar arrays to output the result as an interpolation processing result of the first interpolation processing circuit 20a.

Otherwise, if the circuit 20a judges that one is not a value of "192 to 255 ($+\pi/2$ to $+\pi$): darker blue side", and the other is not a value of "0 to 63 ($-\pi$ to $-\pi/2$): darker red side", then the data identifying unit 51 (see FIG. 3) outputs two scalar arrays of velocity data to the data interpolating unit 53 (see FIG. 3) without causing the data converting unit 52 (see FIG. 3) to perform conversion processing. In that case, the data interpolating unit 53 interpolates the velocity data based on vector operation on complex spaces in the scalar arrays to output the result as an interpolation processing result of the first interpolation processing circuit 20a, as shown in FIGS. 12 and 13, for example.

As described in the above, according to the present embodiment, after the data identifying unit 51 determines a value of velocity data, the data converting unit 52, the data interpolating unit 53 and the data reconverting unit 54 switch between vector operation on a complex space based on a scalar array and vector operation on the complex space based on a color palette array to execute interpolation processing. As such, according to the present embodiment, aliasing disadvantages in interpolation processing on velocity data can be surely solved using an interpolating circuit of known and simple conventional circuit configuration through simple numeric value determination processing.

The present invention is not limited to the above embodiment, but various changes or modifications are possible without departing from the scope of the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:
1. An ultrasonic Doppler diagnosis device comprising:
an ultrasonic transceiver unit configured to transmit an ultrasonic signal for scanning a kinetic reflector and to receive a reflected ultrasonic signal reflected from the kinetic reflector;
a velocity data calculating unit configured to extract a Doppler shift signal using the reflected ultrasonic signal received by the ultrasonic transceiver section, and to calculate velocity data at intersections of sound lines and scanning lines of the kinetic reflector, wherein the velocity data is unsigned numeric data;
a velocity data interpolating unit configured to generate interpolated velocity data for interpolating velocity data between two of the sound lines and two of the scanning lines, using the velocity data at the intersections; and a color image generating unit configured to generate a color flow mapping image of the kinetic reflector based on the velocity data and the interpolated velocity data, wherein the velocity data interpolating unit is comprised of:

a receiving and identifying unit configured to receive a first numeric value and a second numeric value selected from a plurality of values of the velocity data, and to identify whether one of the first numeric value and the second numeric value is smaller than a first threshold value within a range of positive velocity values and the other of the first numeric value and the second numeric value is greater than a second threshold value within a range of negative velocity value, and a converting and interpolating unit configured, when it is identified that one of the first numeric value and the second numeric value is smaller than a first threshold value within a range of positive velocity values and the other of the first numeric value and the second numeric value is greater than a second threshold value within a range of negative velocity values, to convert the first and second numeric values to signed numeric data and to generate the interpolated velocity data based on the converted signed numeric data.

2. The ultrasonic Doppler diagnosis device according to claim 1, wherein:

a velocity data interpolating group includes the receiving and identifying unit, and the converting and interpolating unit, and the velocity data interpolating unit comprises a hierarchical configuration of a plurality of velocity data interpolating groups configured to generate the interpolated velocity data using the velocity data at four of the intersections which are adjacent to each other.

* * * * *